(12) United States Patent
Mallaby

(10) Patent No.: US 11,497,521 B2
(45) Date of Patent: *Nov. 15, 2022

(54) ASSISTED ASPIRATION CATHETER SYSTEM

(71) Applicant: Walk Vascular, LLC, Irvine, CA (US)

(72) Inventor: Mark Mallaby, Oceanside, CA (US)

(73) Assignee: WALK VASCULAR, LLC, Irvine, CA (US)

( * ) Notice: Subject to any disclaimer, the term of this patent is extended or adjusted under 35 U.S.C. 154(b) by 180 days.

This patent is subject to a terminal disclaimer.

(21) Appl. No.: 16/569,988

(22) Filed: Sep. 13, 2019

(65) Prior Publication Data

US 2020/0015840 A1    Jan. 16, 2020

Related U.S. Application Data

(63) Continuation of application No. 15/341,224, filed on Nov. 2, 2016, now Pat. No. 10,499,944, which is a continuation of application No. 12/250,286, filed on Oct. 13, 2008, now Pat. No. 9,510,854.

(51) Int. Cl.
*A61B 17/3203* (2006.01)
*A61M 1/00* (2006.01)
*A61B 17/22* (2006.01)

(52) U.S. Cl.
CPC ..... *A61B 17/32037* (2013.01); *A61M 1/0058* (2013.01); *A61B 2017/22079* (2013.01); *A61B 2217/005* (2013.01); *A61B 2217/007* (2013.01); *A61M 2205/3317* (2013.01)

(58) Field of Classification Search
CPC .... A61B 17/32037; A61B 2017/22079; A61B 2217/005; A61B 2217/007; A61M 1/0058
See application file for complete search history.

(56) References Cited

U.S. PATENT DOCUMENTS

| | | |
|---|---|---|
| 1,114,268 A | 10/1914 | Kells |
| 1,144,268 A | 6/1915 | Vickery |
| 1,148,093 A | 7/1915 | Kells |
| 2,804,075 A | 8/1957 | Borden |
| 3,429,313 A | 2/1969 | Romanelli |
| 3,494,363 A | 2/1970 | Jackson |
| 3,589,363 A | 6/1971 | Banko et al. |

(Continued)

FOREIGN PATENT DOCUMENTS

| | | |
|---|---|---|
| CN | 1120805 A | 4/1996 |
| CN | 201079629 Y | 7/2008 |

(Continued)

OTHER PUBLICATIONS

"Angiojet Ultra Power Pulse Kit Information for Use", Medrad, Inc., downloaded from internet Jan. 23, 2017.

(Continued)

*Primary Examiner* — Deanna K Hall
(74) *Attorney, Agent, or Firm* — Workman Nydegger; Randy Shen

(57) ABSTRACT

A thrombectomy system comprising an aspiration catheter having an aspiration lumen and a high pressure irrigation lumen, the aspiration catheter having a proximal end and a distal, and a control box fluidly connected to the aspiration catheter and configured to synchronously provide irrigation and vacuum through the aspiration catheter.

20 Claims, 3 Drawing Sheets

(56) References Cited

U.S. PATENT DOCUMENTS

| | | | |
|---|---|---|---|
| 3,620,650 | A | 11/1971 | Shaw |
| 3,631,847 | A | 1/1972 | Hobbs |
| 3,693,613 | A | 9/1972 | Kelman |
| 3,707,967 | A | 1/1973 | Kitrilakis et al. |
| 3,807,401 | A | 4/1974 | Bennett et al. |
| 3,818,913 | A | 6/1974 | Wallach |
| 3,916,892 | A | 11/1975 | Hansen et al. |
| 3,918,453 | A | 11/1975 | Leonard |
| 3,930,505 | A | 1/1976 | Wallach |
| 3,955,573 | A | 5/1976 | Hansen et al. |
| 4,274,411 | A | 6/1981 | Dotson, Jr. |
| 4,299,221 | A | 11/1981 | Phillips et al. |
| 4,465,470 | A | 8/1984 | Kelman |
| 4,573,476 | A | 3/1986 | Ruiz |
| 4,574,812 | A | 3/1986 | Arkans |
| 4,638,539 | A | 1/1987 | Palmer |
| 4,690,672 | A | 9/1987 | Veltrup |
| 4,702,733 | A | 10/1987 | Wright et al. |
| 4,715,853 | A | 12/1987 | Prindle |
| 4,740,203 | A | 4/1988 | Hoskins et al. |
| 4,747,834 | A | 5/1988 | Prindle |
| 4,770,654 | A | 9/1988 | Rogers et al. |
| 4,784,157 | A | 11/1988 | Halls et al. |
| 4,832,685 | A | 5/1989 | Haines |
| 4,883,467 | A | 11/1989 | Franetzki et al. |
| 4,886,507 | A | 12/1989 | Patton et al. |
| 4,898,574 | A | 2/1990 | Uchiyama et al. |
| 4,998,919 | A | 3/1991 | Schnepp-Pesch et al. |
| 5,011,468 | A | 4/1991 | Lundquist et al. |
| 5,057,098 | A | 10/1991 | Zelman |
| 5,064,428 | A | 11/1991 | Cope et al. |
| 5,073,164 | A | 12/1991 | Hollister et al. |
| 5,073,168 | A | 12/1991 | Danforth |
| 5,091,656 | A | 2/1992 | Gahn |
| 5,125,893 | A | 6/1992 | Dryden |
| 5,129,887 | A | 7/1992 | Euteneuer et al. |
| 5,135,482 | A | 8/1992 | Neracher |
| 5,163,433 | A | 11/1992 | Kagawa et al. |
| 5,197,795 | A | 3/1993 | Mudrovich |
| 5,234,407 | A | 8/1993 | Teirstein et al. |
| 5,242,404 | A | 9/1993 | Conley et al. |
| 5,248,297 | A | 9/1993 | Takase |
| 5,254,085 | A | 10/1993 | Cleveland |
| 5,290,247 | A | 3/1994 | Crittenden |
| 5,318,518 | A | 6/1994 | Plechinger et al. |
| 5,320,604 | A | 6/1994 | Walker et al. |
| 5,322,504 | A | 6/1994 | Doherty et al. |
| 5,324,263 | A | 6/1994 | Kraus et al. |
| 5,342,293 | A | 8/1994 | Zanger |
| 5,342,306 | A | 8/1994 | Don Michael |
| 5,356,375 | A | 10/1994 | Higley |
| 5,368,555 | A | 11/1994 | Sussman et al. |
| 5,370,609 | A | 12/1994 | Drasler et al. |
| 5,385,562 | A | 1/1995 | Adams et al. |
| 5,395,315 | A | 3/1995 | Griep |
| 5,403,274 | A | 4/1995 | Cannon |
| 5,403,276 | A | 4/1995 | Schechter et al. |
| 5,413,561 | A | 5/1995 | Fischell et al. |
| 5,419,772 | A | 5/1995 | Teitz et al. |
| 5,421,826 | A | 6/1995 | Crocker et al. |
| 5,429,601 | A | 7/1995 | Conley et al. |
| 5,476,450 | A | 12/1995 | Ruggio |
| 5,478,331 | A | 12/1995 | Heflin et al. |
| 5,486,183 | A | 1/1996 | Middleman et al. |
| 5,490,837 | A | 2/1996 | Blaeser et al. |
| 5,496,267 | A | 3/1996 | Drasler et al. |
| 5,527,274 | A | 6/1996 | Zakko |
| 5,536,242 | A | 7/1996 | Willard et al. |
| 5,538,002 | A | 7/1996 | Boussignac et al. |
| 5,562,692 | A | 10/1996 | Bair |
| 5,577,674 | A | 11/1996 | Altonji et al. |
| 5,605,545 | A | 2/1997 | Nowosielski et al. |
| 5,606,968 | A | 3/1997 | Mang |
| 5,624,394 | A | 4/1997 | Barnitz et al. |
| 5,626,563 | A | 5/1997 | Dodge et al. |
| 5,647,847 | A | 7/1997 | Lafontaine et al. |
| 5,669,876 | A | 9/1997 | Schechter et al. |
| 5,695,507 | A | 12/1997 | Auth et al. |
| 5,713,849 | A | 2/1998 | Bosma et al. |
| 5,713,851 | A | 2/1998 | Boudewijn et al. |
| 5,713,878 | A | 2/1998 | Moutafis et al. |
| 5,730,717 | A | 3/1998 | Gelbfish |
| 5,785,685 | A | 7/1998 | Kugler et al. |
| 5,795,322 | A | 8/1998 | Boudewijn |
| 5,795,332 | A | 8/1998 | Lucas et al. |
| 5,810,770 | A | 9/1998 | Chin et al. |
| 5,827,229 | A | 10/1998 | Auth et al. |
| 5,827,243 | A | 10/1998 | Palestrant |
| 5,833,644 | A | 11/1998 | Zadno-Azizi et al. |
| 5,843,022 | A | 12/1998 | Willard et al. |
| 5,843,051 | A | 12/1998 | Adams et al. |
| 5,853,384 | A | 12/1998 | Bair |
| 5,855,567 | A | 1/1999 | Reesemann |
| 5,868,702 | A | 2/1999 | Stevens et al. |
| 5,871,462 | A | 2/1999 | Yoder et al. |
| 5,885,238 | A | 3/1999 | Stevens et al. |
| 5,885,244 | A | 3/1999 | Leone et al. |
| 5,895,399 | A | 4/1999 | Barbut et al. |
| 5,910,252 | A | 6/1999 | Truitt et al. |
| 5,916,192 | A | 6/1999 | Nita et al. |
| 5,921,958 | A | 7/1999 | Ressemann et al. |
| 5,938,645 | A | 8/1999 | Gordon |
| 5,941,871 | A | 8/1999 | Adams et al. |
| 5,944,686 | A | 8/1999 | Patterson et al. |
| 5,957,901 | A | 9/1999 | Mottola et al. |
| 5,989,210 | A | 11/1999 | Morris et al. |
| 5,989,271 | A | 11/1999 | Bonnette et al. |
| 6,001,112 | A | 12/1999 | Taylor |
| 6,019,728 | A | 2/2000 | Iwata et al. |
| 6,022,336 | A | 2/2000 | Zadno-Azizi et al. |
| 6,090,118 | A | 7/2000 | McGuckin, Jr. |
| 6,096,001 | A | 8/2000 | Drasler et al. |
| 6,126,635 | A | 10/2000 | Simpson et al. |
| 6,129,697 | A | 10/2000 | Drasler et al. |
| 6,129,698 | A | 10/2000 | Beck |
| 6,146,355 | A | 11/2000 | Biggs |
| 6,146,396 | A | 11/2000 | Konya et al. |
| 6,152,909 | A | 11/2000 | Bagaoisan et al. |
| 6,159,230 | A | 12/2000 | Samuels |
| 6,176,844 | B1 | 1/2001 | Lee |
| 6,179,851 | B1 | 1/2001 | Barbut et al. |
| 6,190,357 | B1 | 2/2001 | Ferrari et al. |
| 6,196,989 | B1 | 3/2001 | Padget et al. |
| 6,206,898 | B1 | 3/2001 | Honeycutt et al. |
| 6,216,573 | B1 | 4/2001 | Moutafis et al. |
| 6,224,570 | B1 | 5/2001 | Le et al. |
| 6,258,061 | B1 | 7/2001 | Drasler et al. |
| 6,283,719 | B1 | 9/2001 | Frantz et al. |
| 6,293,960 | B1 | 9/2001 | Ken |
| 6,331,171 | B1 | 12/2001 | Cohen |
| 6,375,635 | B1 | 4/2002 | Moutafis et al. |
| 6,423,032 | B2 | 7/2002 | Parodi |
| 6,454,741 | B1 | 9/2002 | Muni et al. |
| 6,471,683 | B2 | 10/2002 | Drasler et al. |
| 6,481,439 | B1 | 11/2002 | Lewis et al. |
| 6,488,672 | B1 | 12/2002 | Dance et al. |
| 6,508,823 | B1 | 1/2003 | Gonon |
| 6,544,209 | B1 | 4/2003 | Drasler et al. |
| 6,558,366 | B1 | 5/2003 | Drasler et al. |
| 6,558,401 | B1 | 5/2003 | Azizi |
| 6,569,148 | B2 | 5/2003 | Bagaoisan et al. |
| 6,572,578 | B1 | 6/2003 | Blanchard |
| 6,579,270 | B2 | 6/2003 | Sussman et al. |
| 6,585,705 | B1 | 7/2003 | Maginot et al. |
| 6,599,271 | B1 | 7/2003 | Easley |
| 6,615,835 | B1 | 9/2003 | Cise et al. |
| 6,616,679 | B1 | 9/2003 | Khosravi et al. |
| 6,622,367 | B1 | 9/2003 | Bolduc et al. |
| 6,635,034 | B1 | 10/2003 | Cosmescu |
| 6,635,070 | B2 | 10/2003 | Leeflang et al. |
| 6,638,235 | B2 | 10/2003 | Miller et al. |
| 6,652,546 | B1 | 11/2003 | Nash et al. |
| 6,669,710 | B2 | 12/2003 | Moutafis et al. |
| 6,676,637 | B1 | 1/2004 | Bonnette et al. |

(56) References Cited

U.S. PATENT DOCUMENTS

| | | |
|---|---|---|
| 6,719,717 B1 | 4/2004 | Johnson et al. |
| 6,723,081 B1 | 4/2004 | Hektner |
| 6,755,803 B1 | 6/2004 | Le et al. |
| 6,755,812 B2 | 6/2004 | Peterson et al. |
| 6,805,684 B2 | 10/2004 | Bonnette et al. |
| 6,818,001 B2 | 11/2004 | Wulfman et al. |
| 6,875,193 B1 | 4/2005 | Bonnette et al. |
| 6,899,712 B2 | 5/2005 | Moutafis et al. |
| 6,926,726 B2 | 8/2005 | Drasler et al. |
| 6,958,059 B2 | 10/2005 | Zadno-Azizi |
| 6,984,239 B1 | 1/2006 | Drasler et al. |
| 6,986,778 B2 | 1/2006 | Zadno-Azizi |
| 6,991,625 B1 | 1/2006 | Gately et al. |
| 7,008,434 B2 | 3/2006 | Kurz et al. |
| 7,044,958 B2 | 5/2006 | Douk et al. |
| 7,122,017 B2 | 10/2006 | Moutafis et al. |
| 7,232,452 B2 | 6/2007 | Adams et al. |
| 7,374,560 B2 | 5/2008 | Ressemann et al. |
| 7,431,711 B2 | 10/2008 | Moutafis et al. |
| 7,479,147 B2 | 1/2009 | Honeycutt et al. |
| 7,481,222 B2 | 1/2009 | Reissmann |
| 7,588,033 B2 | 9/2009 | Wondka |
| 7,591,816 B2 | 9/2009 | Wang et al. |
| 7,604,612 B2 | 10/2009 | Ressemann et al. |
| 7,621,886 B2 | 11/2009 | Burnett |
| 7,654,996 B2 | 2/2010 | Lynn |
| 7,666,161 B2 | 2/2010 | Nash et al. |
| 7,699,804 B2 | 4/2010 | Barry et al. |
| 7,717,685 B2 | 5/2010 | Moutafis et al. |
| 7,717,898 B2 | 5/2010 | Gately et al. |
| 7,736,355 B2 | 6/2010 | Itou et al. |
| 7,753,868 B2 | 7/2010 | Hoffa |
| 7,753,880 B2 | 7/2010 | Malackowski |
| 7,776,005 B2 | 8/2010 | Haggstrom et al. |
| 7,798,996 B1 | 9/2010 | Haddad et al. |
| 7,798,999 B2 | 9/2010 | Bailey et al. |
| 7,806,864 B2 | 10/2010 | Haddad et al. |
| 7,833,239 B2 | 11/2010 | Nash |
| 7,842,055 B2 | 11/2010 | Pintor et al. |
| 7,846,175 B2 | 12/2010 | Bonnette et al. |
| 7,867,192 B2 | 1/2011 | Bowman et al. |
| 7,875,004 B2 | 1/2011 | Yodfat et al. |
| 7,879,022 B2 | 2/2011 | Bonnette et al. |
| 7,887,510 B2 | 2/2011 | Karpowicz et al. |
| 7,905,710 B2 | 3/2011 | Wang et al. |
| 7,909,810 B2 | 3/2011 | Noone |
| 7,914,482 B2 | 3/2011 | Urich et al. |
| 7,914,549 B2 | 3/2011 | Morsi |
| 7,918,654 B2 | 4/2011 | Adahan |
| 7,918,822 B2 | 4/2011 | Kumar et al. |
| 7,918,835 B2 | 4/2011 | Callahan et al. |
| 7,935,077 B2 | 5/2011 | Thor et al. |
| 7,951,073 B2 | 5/2011 | Freed |
| 7,951,107 B2 | 5/2011 | Staid et al. |
| 7,951,112 B2 | 5/2011 | Patzer |
| 7,959,603 B2 | 6/2011 | Wahr et al. |
| 7,981,129 B2 | 7/2011 | Nash et al. |
| 7,998,114 B2 | 8/2011 | Lombardi |
| 8,007,490 B2 | 8/2011 | Schaeffer et al. |
| 8,012,766 B2 | 9/2011 | Graham |
| 8,021,351 B2 | 9/2011 | Boldenow et al. |
| 8,034,018 B2 | 10/2011 | Lutwyche |
| 8,043,313 B2 | 10/2011 | Krolik et al. |
| 8,062,246 B2 | 11/2011 | Moutafis et al. |
| 8,062,257 B2 | 11/2011 | Moberg et al. |
| 8,065,096 B2 | 11/2011 | Moberg et al. |
| 8,066,677 B2 | 11/2011 | Lunn et al. |
| 8,070,694 B2 | 12/2011 | Galdonik et al. |
| 8,075,546 B2 | 12/2011 | Carlisle et al. |
| 8,092,483 B2 | 1/2012 | Galdonik et al. |
| 8,123,777 B2 | 2/2012 | Krolik et al. |
| 8,140,146 B2 | 3/2012 | Kim et al. |
| 8,152,782 B2 | 4/2012 | Jang et al. |
| 8,152,951 B2 | 4/2012 | Zawacki et al. |
| 8,157,787 B2 | 4/2012 | Nash et al. |
| 8,162,877 B2 | 4/2012 | Bonnette et al. |
| 8,162,966 B2 | 4/2012 | Connor et al. |
| 8,177,739 B2 | 5/2012 | Cartledge et al. |
| 8,182,462 B2 | 5/2012 | Istoc et al. |
| 8,187,228 B2 | 5/2012 | Bikovsky |
| 8,202,243 B2 | 6/2012 | Morgan |
| 8,209,060 B2 | 6/2012 | Ledford |
| 8,221,348 B2 | 7/2012 | Hackett et al. |
| 8,246,573 B2 | 8/2012 | Ali et al. |
| 8,246,580 B2 | 8/2012 | Hopkins et al. |
| 8,257,298 B2 | 9/2012 | Hamboly |
| 8,257,343 B2 | 9/2012 | Chan et al. |
| 8,262,645 B2 | 9/2012 | Bagwell et al. |
| 8,267,893 B2 | 9/2012 | Moberg et al. |
| 8,287,485 B2 | 10/2012 | Kimura et al. |
| 8,291,337 B2 | 10/2012 | Gannin et al. |
| 8,292,841 B2 | 10/2012 | Gregersen |
| 8,308,745 B2 | 11/2012 | Seto et al. |
| 8,317,739 B2 | 11/2012 | Kueebler |
| 8,317,770 B2 | 11/2012 | Miesel et al. |
| 8,317,773 B2 | 11/2012 | Appling et al. |
| 8,317,786 B2 | 11/2012 | Dahla et al. |
| 8,323,268 B2 | 12/2012 | Ring et al. |
| 8,337,175 B2 | 12/2012 | Dion et al. |
| 8,337,451 B2 | 12/2012 | Lareau et al. |
| 8,343,097 B2 | 1/2013 | Pile-Spellman et al. |
| 8,343,131 B2 | 1/2013 | Vinten-Johansen |
| 8,348,896 B2 | 1/2013 | Wagner |
| 8,353,858 B2 | 1/2013 | Kozak et al. |
| 8,353,860 B2 | 1/2013 | Boulais et al. |
| 8,357,138 B2 | 1/2013 | Pierpont et al. |
| 8,372,038 B2 | 2/2013 | Urich et al. |
| 8,398,579 B2 | 3/2013 | Morris et al. |
| 8,398,581 B2 | 3/2013 | Panotopoulos |
| 8,398,582 B2 | 3/2013 | Gordon et al. |
| 8,414,521 B2 | 4/2013 | Baker et al. |
| 8,414,522 B2 | 4/2013 | Kamen et al. |
| 8,419,709 B2 | 4/2013 | Haddad et al. |
| 8,425,458 B2 | 4/2013 | Scopton |
| 8,430,837 B2 | 4/2013 | Jenson et al. |
| 8,430,845 B2 | 4/2013 | Wahr et al. |
| 8,430,861 B2 | 4/2013 | Schwartz et al. |
| 8,439,876 B2 | 5/2013 | Spohn et al. |
| 8,454,557 B1 | 6/2013 | Qi et al. |
| 8,465,456 B2 | 6/2013 | Stivland |
| 8,465,867 B2 | 6/2013 | Kim |
| 8,483,980 B2 | 7/2013 | Moberg et al. |
| 8,491,523 B2 | 7/2013 | Thor et al. |
| 8,506,537 B2 | 8/2013 | Torstensen et al. |
| 8,523,801 B2 | 9/2013 | Nash et al. |
| 8,529,498 B2 | 9/2013 | Moutafis et al. |
| 8,545,432 B2 | 10/2013 | Renati et al. |
| 8,562,555 B2 | 10/2013 | MacMahon et al. |
| 8,579,926 B2 | 11/2013 | Pintor et al. |
| 8,597,238 B2 | 12/2013 | Bonnette et al. |
| 8,608,699 B2 | 12/2013 | Blomquist |
| 8,613,618 B2 | 12/2013 | Brokx |
| 8,613,724 B2 | 12/2013 | Lanier et al. |
| 8,617,110 B2 | 12/2013 | Moberg et al. |
| 8,617,127 B2 | 12/2013 | Woolston et al. |
| 8,623,039 B2 | 1/2014 | Seto et al. |
| 8,641,671 B2 | 2/2014 | Michaud et al. |
| 8,647,294 B2 | 2/2014 | Bonnette et al. |
| 8,652,086 B2 | 2/2014 | Gerg et al. |
| 8,657,777 B2 | 2/2014 | Kozak et al. |
| 8,657,785 B2 | 2/2014 | Torrance et al. |
| 8,668,464 B2 | 3/2014 | Kensy et al. |
| 8,668,665 B2 | 3/2014 | Gerg et al. |
| 8,670,836 B2 | 3/2014 | Aeschlimann et al. |
| 8,672,876 B2 | 3/2014 | Jacobson et al. |
| 8,681,010 B2 | 3/2014 | Moberg et al. |
| 8,715,237 B2 | 5/2014 | Moberg et al. |
| 8,721,674 B2 | 5/2014 | Kusleika |
| 8,758,325 B2 | 6/2014 | Webster et al. |
| 8,783,151 B1 | 7/2014 | Janardhan et al. |
| 8,803,030 B1 | 8/2014 | Janardhan et al. |
| 8,814,892 B2 | 8/2014 | Galdonik et al. |
| 8,851,866 B2 | 10/2014 | Moutafis et al. |
| 8,900,214 B2 | 12/2014 | Nance et al. |

(56) References Cited

U.S. PATENT DOCUMENTS

| | | |
|---|---|---|
| 8,932,320 B1 | 1/2015 | Janardhan et al. |
| 8,932,321 B1 | 1/2015 | Janardhan et al. |
| 8,936,447 B2 | 1/2015 | Abal |
| 8,945,030 B2 | 2/2015 | Weston |
| 8,962,561 B2 | 2/2015 | Shalgi et al. |
| 8,974,418 B2 | 3/2015 | Bonnette et al. |
| 8,979,798 B2 | 3/2015 | Shener et al. |
| 8,986,252 B2 | 3/2015 | Cummings et al. |
| 8,998,843 B2 | 4/2015 | Bonnette et al. |
| 9,011,114 B2 | 4/2015 | Farrell et al. |
| 9,024,768 B2 | 5/2015 | Mandro et al. |
| 9,033,925 B2 | 5/2015 | Moberg et al. |
| 9,042,938 B2 | 5/2015 | Nimbalker et al. |
| 9,078,691 B2 | 7/2015 | Morris et al. |
| 9,238,122 B2 | 1/2016 | Malhi et al. |
| 9,254,144 B2 | 2/2016 | Nguyen et al. |
| 9,278,189 B2 | 3/2016 | Corbett |
| 9,358,035 B2 | 6/2016 | Kojima |
| 9,402,938 B2 | 8/2016 | Aklog et al. |
| 9,510,854 B2 * | 12/2016 | Mallaby .............. A61M 1/0058 |
| 9,586,023 B2 | 3/2017 | Bonnette et al. |
| 9,592,073 B2 | 3/2017 | Kojima et al. |
| 9,597,480 B2 | 3/2017 | Purdy et al. |
| 9,693,789 B2 | 7/2017 | Garrison et al. |
| 9,770,551 B1 | 9/2017 | Faden |
| 9,782,195 B2 | 10/2017 | MacTaggart et al. |
| 9,808,266 B2 | 11/2017 | Ray et al. |
| 9,827,404 B2 | 11/2017 | Nance et al. |
| 9,833,257 B2 | 12/2017 | Bonnette et al. |
| 9,883,877 B2 | 2/2018 | Look et al. |
| 10,238,853 B2 | 3/2019 | Kume et al. |
| 10,383,983 B2 | 8/2019 | Aklog et al. |
| 10,390,926 B2 | 8/2019 | Janardhan et al. |
| 10,426,885 B2 | 10/2019 | Criado et al. |
| 10,499,944 B2 * | 12/2019 | Mallaby .............. A61M 1/0058 |
| 10,531,883 B1 | 1/2020 | Deville et al. |
| 2001/0051811 A1 | 12/2001 | Bonnette et al. |
| 2002/0016564 A1 | 2/2002 | Courtney et al. |
| 2002/0058904 A1 | 5/2002 | Boock et al. |
| 2002/0068895 A1 | 6/2002 | Beck |
| 2002/0133114 A1 | 9/2002 | Itoh et al. |
| 2002/0138095 A1 | 9/2002 | Mazzocchi et al. |
| 2002/0165575 A1 | 11/2002 | Saleh |
| 2002/0173819 A1 | 11/2002 | Leeflang et al. |
| 2002/0176788 A1 | 11/2002 | Moutafis et al. |
| 2003/0032918 A1 | 2/2003 | Quinn |
| 2003/0055404 A1 | 3/2003 | Moutafis |
| 2003/0069549 A1 | 4/2003 | MacMahon et al. |
| 2003/0083681 A1 | 5/2003 | Moutafis et al. |
| 2003/0088209 A1 | 5/2003 | Chiu et al. |
| 2003/0144688 A1 | 7/2003 | Brady et al. |
| 2003/0216760 A1 | 11/2003 | Welch et al. |
| 2003/0220556 A1 | 11/2003 | Porat et al. |
| 2003/0236533 A1 | 12/2003 | Wilson et al. |
| 2004/0030281 A1 | 2/2004 | Goble et al. |
| 2004/0049225 A1 | 3/2004 | Denison |
| 2004/0082915 A1 | 4/2004 | Kadan |
| 2004/0087988 A1 | 5/2004 | Heitzmann et al. |
| 2004/0143225 A1 | 7/2004 | Callan et al. |
| 2004/0147871 A1 | 7/2004 | Burnett |
| 2004/0153109 A1 | 8/2004 | Tiedtke et al. |
| 2004/0158136 A1 | 8/2004 | Gough et al. |
| 2004/0167463 A1 | 8/2004 | Zawacki et al. |
| 2004/0193046 A1 | 9/2004 | Nash et al. |
| 2004/0199201 A1 | 10/2004 | Kellett et al. |
| 2004/0243157 A1 | 12/2004 | Connor et al. |
| 2005/0043682 A1 | 2/2005 | Kucklick et al. |
| 2005/0049547 A1 | 3/2005 | Anspach et al. |
| 2005/0065426 A1 | 3/2005 | Porat et al. |
| 2005/0085769 A1 | 4/2005 | MacMahon et al. |
| 2005/0102165 A1 | 5/2005 | Oshita et al. |
| 2005/0159716 A1 | 7/2005 | Kobayashi et al. |
| 2005/0196748 A1 | 9/2005 | Ericson |
| 2005/0238503 A1 | 10/2005 | Rush et al. |
| 2005/0240146 A1 | 10/2005 | Nash et al. |
| 2005/0283150 A1 | 12/2005 | Moutafis et al. |
| 2006/0009785 A1 | 1/2006 | Maitland et al. |
| 2006/0063973 A1 | 3/2006 | Makower et al. |
| 2006/0064051 A1 | 3/2006 | Gross |
| 2006/0064123 A1 | 3/2006 | Bonnette et al. |
| 2006/0093989 A1 | 5/2006 | Hahn et al. |
| 2006/0142630 A1 | 6/2006 | Meretei |
| 2006/0149191 A1 | 7/2006 | DiFiore |
| 2006/0229550 A1 | 10/2006 | Staid et al. |
| 2006/0264808 A1 | 11/2006 | Staid et al. |
| 2007/0073233 A1 | 3/2007 | Thor et al. |
| 2007/0078438 A1 | 4/2007 | Okada |
| 2007/0135812 A1 | 6/2007 | Sartor |
| 2007/0197956 A1 | 8/2007 | Le et al. |
| 2007/0197963 A1 | 8/2007 | Griffiths et al. |
| 2007/0225739 A1 | 9/2007 | Pintor et al. |
| 2007/0249990 A1 | 10/2007 | Cosmescu |
| 2008/0009784 A1 | 1/2008 | Leedle et al. |
| 2008/0091061 A1 | 4/2008 | Kumar et al. |
| 2008/0097339 A1 | 4/2008 | Ranchod et al. |
| 2008/0097563 A1 | 4/2008 | Petrie et al. |
| 2008/0108960 A1 | 5/2008 | Shapland et al. |
| 2008/0125698 A1 | 5/2008 | Gerg et al. |
| 2008/0195058 A1 | 8/2008 | Moutafis et al. |
| 2008/0195139 A1 | 8/2008 | Donald et al. |
| 2008/0243054 A1 | 10/2008 | Mollstam et al. |
| 2008/0243153 A1 | 10/2008 | Nguyen et al. |
| 2008/0249501 A1 | 10/2008 | Yamasaki |
| 2008/0255596 A1 | 10/2008 | Jenson et al. |
| 2008/0294008 A1 | 11/2008 | Toyama |
| 2008/0294181 A1 | 11/2008 | Wensel et al. |
| 2008/0306465 A1 | 12/2008 | Bailey et al. |
| 2008/0319376 A1 | 12/2008 | Wilcox et al. |
| 2009/0048607 A1 | 2/2009 | Rockley |
| 2009/0054825 A1 | 2/2009 | Melsheimer et al. |
| 2009/0105690 A1 | 4/2009 | Schaeffer et al. |
| 2009/0157057 A1 | 6/2009 | Ferren et al. |
| 2009/0292212 A1 | 11/2009 | Ferren et al. |
| 2009/0306476 A1 | 12/2009 | Banik et al. |
| 2009/0306692 A1 | 12/2009 | Barrington et al. |
| 2010/0010524 A1 | 1/2010 | Barrington et al. |
| 2010/0030134 A1 | 2/2010 | Fitzgerald et al. |
| 2010/0030186 A1 | 2/2010 | Stivland |
| 2010/0094201 A1 | 4/2010 | Mallaby |
| 2010/0145302 A1 | 6/2010 | Cull et al. |
| 2010/0191178 A1 | 7/2010 | Ross et al. |
| 2010/0204672 A1 | 8/2010 | Lockhart et al. |
| 2010/0217276 A1 | 8/2010 | Garrison et al. |
| 2010/0228273 A1 | 9/2010 | Staid et al. |
| 2010/0268236 A1 | 10/2010 | Moutafis et al. |
| 2010/0274191 A1 | 10/2010 | Ting |
| 2011/0034986 A1 | 2/2011 | Chou et al. |
| 2011/0091331 A1 | 4/2011 | Moutafis et al. |
| 2011/0092892 A1 | 4/2011 | Nitsan et al. |
| 2011/0106019 A1 | 5/2011 | Bagwell et al. |
| 2011/0160683 A1 | 6/2011 | Pinotti et al. |
| 2011/0282426 A1 | 11/2011 | Mitra et al. |
| 2012/0059340 A1 | 3/2012 | Larsson |
| 2012/0059354 A1 | 3/2012 | Zarate |
| 2012/0065656 A1 | 3/2012 | Karwei |
| 2012/0123509 A1 | 5/2012 | Merrill et al. |
| 2012/0130415 A1 | 5/2012 | Tal et al. |
| 2012/0165756 A1 | 6/2012 | Root et al. |
| 2012/0259265 A1 | 10/2012 | Salehi et al. |
| 2012/0277665 A1 | 11/2012 | Tachoire et al. |
| 2012/0289910 A1 | 11/2012 | Shtul et al. |
| 2012/0291811 A1 | 11/2012 | Dabney et al. |
| 2012/0330196 A1 | 12/2012 | Nita |
| 2013/0085381 A1 | 4/2013 | Comerota et al. |
| 2013/0184734 A1 | 7/2013 | Morris et al. |
| 2013/0190701 A1 | 7/2013 | Kirn |
| 2013/0245543 A1 | 9/2013 | Gerg et al. |
| 2013/0267891 A1 | 10/2013 | Malhi et al. |
| 2013/0281788 A1 | 10/2013 | Garrison |
| 2013/0310845 A1 | 11/2013 | Thor et al. |
| 2013/0331776 A1 | 12/2013 | Klein et al. |
| 2014/0005699 A1 | 1/2014 | Bonnette et al. |
| 2014/0058361 A1 | 2/2014 | Gordon |
| 2014/0147246 A1 | 5/2014 | Chappel et al. |

(56) References Cited

U.S. PATENT DOCUMENTS

| | | |
|---|---|---|
| 2014/0155931 A1 | 6/2014 | Bose et al. |
| 2014/0228569 A1 | 8/2014 | Okumura et al. |
| 2014/0228869 A1 | 8/2014 | Bonnette et al. |
| 2014/0276920 A1 | 9/2014 | Hendrick et al. |
| 2014/0309589 A1 | 10/2014 | Momose et al. |
| 2014/0323906 A1 | 10/2014 | Peatfield et al. |
| 2014/0360494 A1 | 12/2014 | Herskovic |
| 2014/0378951 A1 | 12/2014 | Dye |
| 2015/0025446 A1 | 1/2015 | Jacobson et al. |
| 2015/0032138 A1 | 1/2015 | Jenson et al. |
| 2015/0094673 A1 | 4/2015 | Pratt et al. |
| 2015/0094748 A1 | 4/2015 | Nash et al. |
| 2015/0142030 A1 | 5/2015 | MacTaggart et al. |
| 2015/0257724 A1 | 9/2015 | Lautenschläger |
| 2015/0327875 A1 | 11/2015 | Look et al. |
| 2015/0374391 A1 | 12/2015 | Quick et al. |
| 2016/0051323 A1 | 2/2016 | Stigall et al. |
| 2016/0058614 A1 | 3/2016 | Ross et al. |
| 2016/0143721 A1 | 5/2016 | Rosenbluth et al. |
| 2016/0220741 A1 | 8/2016 | Garrison et al. |
| 2017/0065396 A1 | 3/2017 | Look et al. |
| 2017/0079672 A1 | 3/2017 | Quick |
| 2017/0105745 A1 | 4/2017 | Rosenbluth et al. |
| 2017/0172603 A1 | 6/2017 | Bonnette et al. |
| 2017/0181760 A1 | 6/2017 | Look et al. |
| 2017/0265885 A1 | 9/2017 | Bonnette et al. |
| 2017/0281204 A1 | 10/2017 | Garrison et al. |
| 2017/0290598 A1 | 10/2017 | Culbert et al. |
| 2018/0207397 A1 | 7/2018 | Look et al. |
| 2018/0214172 A1 | 8/2018 | Donnelly et al. |
| 2018/0338770 A1 | 11/2018 | Mogi et al. |
| 2020/0345904 A1 | 11/2020 | Casey et al. |
| 2020/0367917 A1 | 11/2020 | Teigen et al. |

FOREIGN PATENT DOCUMENTS

| | | |
|---|---|---|
| CN | 201603160 U | 10/2010 |
| CN | 103767760 A | 5/2014 |
| DE | 3715418 A1 | 11/1987 |
| DE | 4018736 A1 | 1/1992 |
| EP | 0726466 A1 | 8/1996 |
| EP | 806213 A1 | 11/1997 |
| EP | 1092396 A2 | 4/2001 |
| EP | 1488748 A1 | 12/2004 |
| EP | 2859902 A1 | 4/2015 |
| EP | 2131759 B1 | 10/2017 |
| JP | 06-125915 A | 5/1994 |
| JP | 06-205784 A | 7/1994 |
| JP | 06-205785 A | 7/1994 |
| JP | 07-299078 A | 11/1995 |
| JP | 2001-161700 A | 6/2001 |
| JP | 2003-010194 A | 1/2003 |
| JP | 2003-101194 A | 4/2003 |
| JP | 2003-514632 A | 4/2003 |
| JP | 2003-260127 A | 9/2003 |
| JP | 2003-290236 A | 10/2003 |
| JP | 2004-514466 A | 5/2004 |
| JP | 2007-160109 A | 6/2007 |
| JP | 2009-039216 A | 2/2009 |
| JP | 2013-154171 A | 8/2013 |
| JP | 2013-180156 A | 9/2013 |
| WO | 90/05493 A1 | 5/1990 |
| WO | 96/01079 A1 | 1/1996 |
| WO | 99601079 A1 | 1/1996 |
| WO | 96/35469 A1 | 11/1996 |
| WO | 99/18850 A1 | 4/1999 |
| WO | 00/69348 A1 | 11/2000 |
| WO | 01/37916 A1 | 5/2001 |
| WO | 02/19928 A2 | 3/2002 |
| WO | 02/26289 A1 | 4/2002 |
| WO | 2004100772 A2 | 11/2004 |
| WO | 2007/087404 A2 | 8/2007 |
| WO | 2007/143633 A2 | 12/2007 |
| WO | 2008097993 A2 | 8/2008 |
| WO | 2008/121481 A1 | 10/2008 |
| WO | 2015/179329 A1 | 11/2015 |
| WO | 2016/126974 A1 | 8/2016 |
| WO | 2018/215840 A1 | 11/2018 |

OTHER PUBLICATIONS

Comparison of Dimensions and Aspiration Rate of the Pronto V3, Pronto LP, Export XT, Export AP, Fetch, Xtract, Diver C.E, and QuickCat Catheter, Vascular Solutions, Inc., downloaded from internet Oct. 22, 2014.

Dalal, J., Sahoo, P., Dhall, A., Kapoor, R., Krishnamurthy, A., Shetty, S., Trivedi, S., Kahali, D., Shah, B., Chockalingam, K., Abdullakutty, J., Shetty, P., Chopra, A., Ray, R., Desai, D., Pachiyappan, Ratnaparkhi, G., Sharma, M., Sambasivam, K. "Role of thrombysis in reperfusion therapy for management of AMI: Indian scenario," Indian Heart Journal, 2013, pp. 566-585, vol. 63, Cardiological Society of India, Bombay, India.

Franetzki, M., "Confusion in the Terminology of Insulin Devices", Diabetes Care, Jan.-Feb. 1982, pp. 74-75, vol. 5, No. 1, American Diabetes Association, Alexandria, USA.

Frolich, G., Meier, P., White, S., Yellon, D., Hausenloy, D., "Myocardial reperfusion injury: looking beyond primary PCI", European Heart Journal Jun. 2013, pp. 1714-1722, vol. 34, No. 23, Elsevier, Amsterdam, The Netherlands.

Gousios, A, Shearn, M, "Effect of Intravenous Heparin on Human Blood Viscosity", Circulation, Dec. 1959, pp. 1063-1066, vol. 20, American Heart Association, Dallas, USA.

Harvard Health; Normal Body Temperature: Rethinking the normal human body temperature; p. 1; published Apr. 1, 2006; http://www.health.harvard.edu/press.sub.-releases/normal.sub-body.sub.--temperature.

Infusion Liquid Flow Sensors—Safe, Precise and Reliable, Sensirion, downloaded from Internet Apr. 3, 2015.

Irsigler, K, Kritz, H., Hagmuller, G., Franezki, M., Prestele, K, Thurow, H., Geisen, K., "Long-term Continuous Intraperitoneal Insulin Infusion with an Implanted Remote-Controlled Insulin Infusion Device", Diabetes, Dec. 1981, pp. 1072-1075, vol. 30, No. 12, American Diabetes Association, New York, USA.

Kritz, H., Hagmuller, G, Lovett, R., Irsigler, K., "Implanted Constant Basal Rate Insulin Infusion Devices for Type 1 (Insulin-Dependent) Diabetic Patients", Diabetologia, Aug. 1983, pp. 78-81, vol. 25, No. 2, Springer-Verlag, Berlin, Germany.

Lipinski, M., Lee, R., Gaglia, M., Torguson, R., Garcia-Garcia, H., Pichard, A., Satler, L., Waksman, R. "Comparison of heparin, bivalirudin, and different glycoprotein IIb/IIIa inhibitor regimens for anticoagulation during percutaneous coronary intervention: A network meta-analysis," Cardiovascular Revascularization Medicine, 2016, pp. 535-545, vol. 17, Elsevier, New York, USA.

Makes even the most difficult intervention a Fast and Smooth Run. GuideLiner brochure. Vascular Solutions,. Inc., downloaded from internet Apr. 9, 2015.

Metzler, L., "Miniature Sensor Combines with Micropump to Control Drug Delivery", Medical Design Technology, Mar. 2017, pp. 22-23, MDTmag.com, Advantage Business Media, Rockaway, USA.

Micossi, P., Cristallo, M., Galiberti, G, Librenti, M., Petrella, G., Hozza, G., Hutter, K., Babic, D., Hagmuller, G., Vert, F., Irsigler, K., Walter, H., Ladik, T., Flaschentrager, T., Gunther, A., Kronski, K., Mehnert, H., Bauersachs, R., Ruhland, B., Piwernetz, K., Renner, R., Hepp, K., Buchholz, G., Kollert, D., Wohlers, C, Jahrling, P., Franetzki, M., Pfeiffer, C., Neuhauser, C., Seipke. G., Deutschlander. N., Zoltobrocki, M., "One-Year Trial of a Remote-Controlled Implantable Insulin Infusion System in Type I Diabetic Patients", The Lancet, Oct. 15, 1988, pp. 866-869, vol. 2, No.

Parikh, A., Ali, F., "Novel Use of GuideLiner Catheter to Perform Aspiration Thrombectomy in a Saphenous Vein Graft" Cath Lab Digest, Oct. 2013, downloaded from internet Oct. 22, 2014.

Pechlaner, C., Knapp, E., Wiedermann, C. "Hypersensitivity reactions associated with recombinant tissue-type plasminogen activator and urokinase," Blood Coagulation and Fibrinolysis, 2001, pp. 491-494, vol. 12, Lippincott Williams & Wilkins, Hagerstown, USA.

(56) References Cited

OTHER PUBLICATIONS

Prasad, A., Stone, G., Holmes, D., Gersh, B., Peperfusion Injury, Microvascular Dysfunction, and Carioprotection: The "Dark Side" of Reperfusion, Circulation, Nov. 24, 2009, pp. 2105-2112, vol. 120, American Heart Association, Dallas, USA.

Principles and Practice of Pharmacology for Anaesthetists, ed. Calvey, T., Williams, N., 2008, pp. 324-327, 5th Edition, Blackwell Publishing, Malden, USA.

Puddu, P., Ianetta, L., Placanica, A., Cuturello, D., Schiariti, M., Manfrini, O., "The role of Glycoprotein IIb/IIIa inhibitors in acute coronary syndromes and the interference with anemia," International Journal of Cardiology, 2016, pp. 1091-1096, vol. 222, Elsevier, Amsterdam, The Netherlands.

Rodriquez, R., Conde-Green, A., "Quantification of Negative Pressures Generated by Syringes of Different Calibers Used for Liposuction", Plastic & Reconstructive Surgery, Aug. 2012; p. 383e-384e, vol. 130, No. 2, Lippicott Williams & Wilkins, Philadelphia, USA.

Saudek, C., Selam, J-L, Pitt, H., Waxman, K., Rubio, M., Jeandidier, N., Turner, D., Fischell, R., Charles, M., "A Preliminary trial of the Programmable Implantable Medication System for Insulin Delivery", The New England Journal of Medicine, Aug. 31, 1989, pp. 574-579, vol. 321, No. 9, Massachusetts Medical Society, Boston, USA.

Selam, J-L, "Development of Implantable Insulin Pumps: Long is the Road", Diabetic Medicine, Nov. 1988, pp. 724-733, vol. 5, No. 8, Wiley, Chichester, UK.

Stys, A., Stys, T., Rajpurohit, N., Khan, M. "A Novel Application of GuideLiner Catheter for Thrombectomy in Acute Myocardial Infarction: A Case Series", Journal of Invasive cardiology, Nov. 2013, pp. 620-624, vol. 25, No. 11, King of Prussia, USA.

Van De Werf, F, "zthe ideal fibrinolytic: can drug design improve clinical results?" European Heart Journal, 1999, pp. 1452-1458, vol. 20, Elsevier, Amsterdam, The Netherlands.

Warmerdam, P., Vanderlick, K., Vandervoort, P., de Smedt, H., Plaisance, S., De Maeyer, M., Collen, D. "Saphylokinase-Specific-Cell-Mediated Immunity in Humans," The Journal of Immunology, 2002, pp. 155-161, vol. 168, Williams & Wilkins Co., Baltimore, USA.

\* cited by examiner

ASSISTED ASPIRATION CATHETER SYSTEM

RELATED APPLICATIONS

This application is a continuation of U.S. application Ser. No. 15/341,224, filed Nov. 2, 2016, which is a continuation of U.S. application Ser. No. 12/250,286, filed Oct. 13, 2008, now U.S. Pat. No. 9,510,854, the entirety disclosures of which are incorporated herein by reference.

TECHNICAL FIELD

The present disclosure pertains generally to medical devices and methods of their use. More particularly, the present invention pertains to aspiration and thrombectomy devices and methods of use thereof.

BACKGROUND

Several devices and systems already exist to aid in the removal of thrombetic material. These include simple aspiration tube type devices using vacuum syringes to extract thrombus into the syringe, simple flush-and-aspirate devices, more complex devices with rotating components the pull in, macerate and transport thrombetic material away from the distal tip using a mechanical auger, systems that use very high pressure to macerate the thrombus and create a venturi effect to flush the macerated material away.

All of the devices described above have limitations as a result of individual design characteristics. For example, simple aspiration catheters off ease of use and rapid deployment but may become blocked or otherwise inoperable when faced with older, more organized throbetic material. Such devices must be removed and cleared outside the body and then re-inserted into the vasculature, which lengthens the time needed for the procedure and increases the opportunity to kink the catheter shaft. Such kinks may reduce performance by decreasing the cross-sectional area of the catheter or may render the device inoperable. The use of a syringe to provide vacuum, moreover, may increase the risk of operator error by not preventing the operator from applying positive pressure to the aspiration lumen and thereby expelling loose embolic material into the patient vasculature.

Mechanical rotary devices use an auger to grab and carry the thrombus away from the target area. Some create transport force via vacuum bottles while others create differential pressure at the distal tip of the device with the auger acting as a low pressure pump. These devices typically work slowly and offer the physician no feedback as to when the device should be advanced further into the lesion.

Flushing type devices include manual flush type devices in which the physician manipulates a hand-driven pump to provide flowing saline at the tip of the device to break up and aspirate the thrombus material, which may introduce performance variations based on the ability of the physician to consistently pump the device over the duration of the procedure. Flushing devices also include high pressure flushing devices that macerate the thrombus and then, using a vortex created by the high pressure fluid, transport the emulsified thrombetic material to a collection bag. These devices are effective at removing all levels of thrombetic material, but the pressure created by the device is so great that its action against certain vessel walls may interrupt the heart muscle stimulation mechanism and creates a brady-chardia event in certain patients that requires a pacing lead to be placed in the patient prior to use. Further, interacting with the thrombetic material outside of the catheter may allow loose material to escape the capture mechanism.

Thus, a need remains for improved thrombus removal capability particularly for systems that have increased reliability, are more benign and offer greater feedback capabilities.

SUMMARY

The disclosure pertains generally to devices such as an assisted aspiration catheter for removing a range of thrombetic material from the general vascular system, natural or synthetic tubule or cavity found in the human body of a patient via standard vascular access using the Seldinger technique.

In one illustrative but non-limiting example, a vacuum source is connected to the proximal end of a flexible, kink resistant tube or aspiration lumen or catheter. The other end of the aspiration lumen is open to patient vasculature to allow thrombetic material to be drawn into the aspiration lumen via the suction provided by the vacuum source. The vacuum source may also act as a containment vessel for aspirated thrombetic material. A second flexible tube that may be housed inside the aspiration lumen conveys a pressurized stream of sterile saline or other physiologic solution to a specifically placed orifice near the distal end of the aspiration lumen. A control system may be provided that ensures the synchronous operation of the vacuum source and the pressurized stream. Thereby thrombetic material may be drawn by vacuum into the distal opening of the catheter. Less organized thrombetic material may be immediately aspirated into the containment vessel and more organized thrombetic material may be removed by being drawn into the catheter and is macerated by a high-pressure fluid stream within the catheter opening and aspirated into the containment vessel.

The above summer summary of some embodiments is not intended to describe each disclosed embodiment or every implementation of the present invention. The Figures and Detailed Description that follow more particularly exemplify these embodiments.

Figure 1:
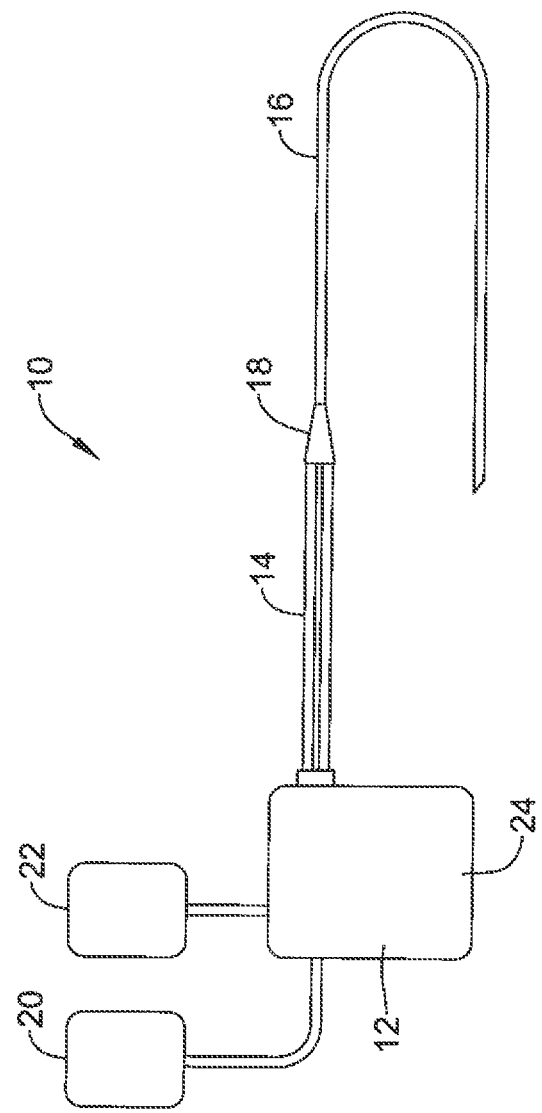
FIG. 1 is a diagrammatic view of as assisted aspiration catheter system 10.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the claims.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a diagrammatic figure depicting assisted aspiration system 10. Aspiration system 10 includes a remote hand piece 12 that contains the fluid pump and the operator control interface. In one contemplated embodiment, system 10 is a single use disposable unit. Aspiration system 10 may also include extension tubing 14, which contains lumens both for fluid irrigation and for aspiration, and which allows independent manipulation of a catheter 16 without requiring repositioning of hand piece 12 during the procedure. Extension tubing 14 may also act as a pressure accumulator. High pressure fluid flow from the displacement pump pulses with each stroke of the pump creating a sinusoidal pressure map with distinct variations between the peaks and valleys of each sine wave. Extension tubing 14 may be matched to the pump to expand and contract in unison with each pump pulse to reduce the variation in pressure caused by the pump pulses to produce a smooth or smoother fluid flow at tip of catheter 16. Any tubing having suitable compliancy characteristics may be used. The extension tubing may be permanently attached to the pump or it may be attached to the pump by a connector. The connector is preferably configured to ensure that the extension tubing cannot be attached to the pump incorrectly.

An interface connector 18 joins extension tubing 14 and catheter 16 together. In one contemplated embodiment, interface connector 18 may contain a filter assembly (not shown) between high pressure extension tubing 16 and the high pressure lumen of catheter 16. The catheter and extension tube may be permanently joined by connector 18. Alternatively, interface connector 18 may contain a standardized connection so that a selected catheter 16 may be attached to extension tubing 14.

Attached to hand piece 12 are a fluid source 20 and a vacuum source 22. A standard hospital saline bag may be used as fluid source 20; such bags are readily available to the physician and provide the necessary volume to perform the procedure. Vacuum bottles may provide the vacuum source 22 or the vacuum source may be provided by a syringe, a vacuum pump or other suitable vacuum source.

In one contemplated embodiment, catheter 16 has a variable stiffness ranging from stiffer at the proximal end to more flexible at the distal end. The variation in the stiffness of catheter 16 may be achieved with a single tube with no radial bonds between two adjacent tubing pieces. For example, the shaft of catheter 16 may be made from a single length of metal tube that has a spiral cut down the length of the tube to provide shaft flexibility. Variable stiffness may be created by varying the pitch of the spiral cut through different lengths of the metal tube. For example, the pitch of the spiral cut may be greater (where the turns of the spiral cut are closer together) at the distal end of the device to provide greater flexibility. Conversely, the pitch of the spiral cut at the proximal end may be lower (where the turns of the spiral cut are further apart) to provide increased stiffness. A single jacket covers the length of the metal tube to provide for a vacuum tight catheter shaft. Other features of catheter 16 are described with reference to FIG. 3, below.

Figure 2:
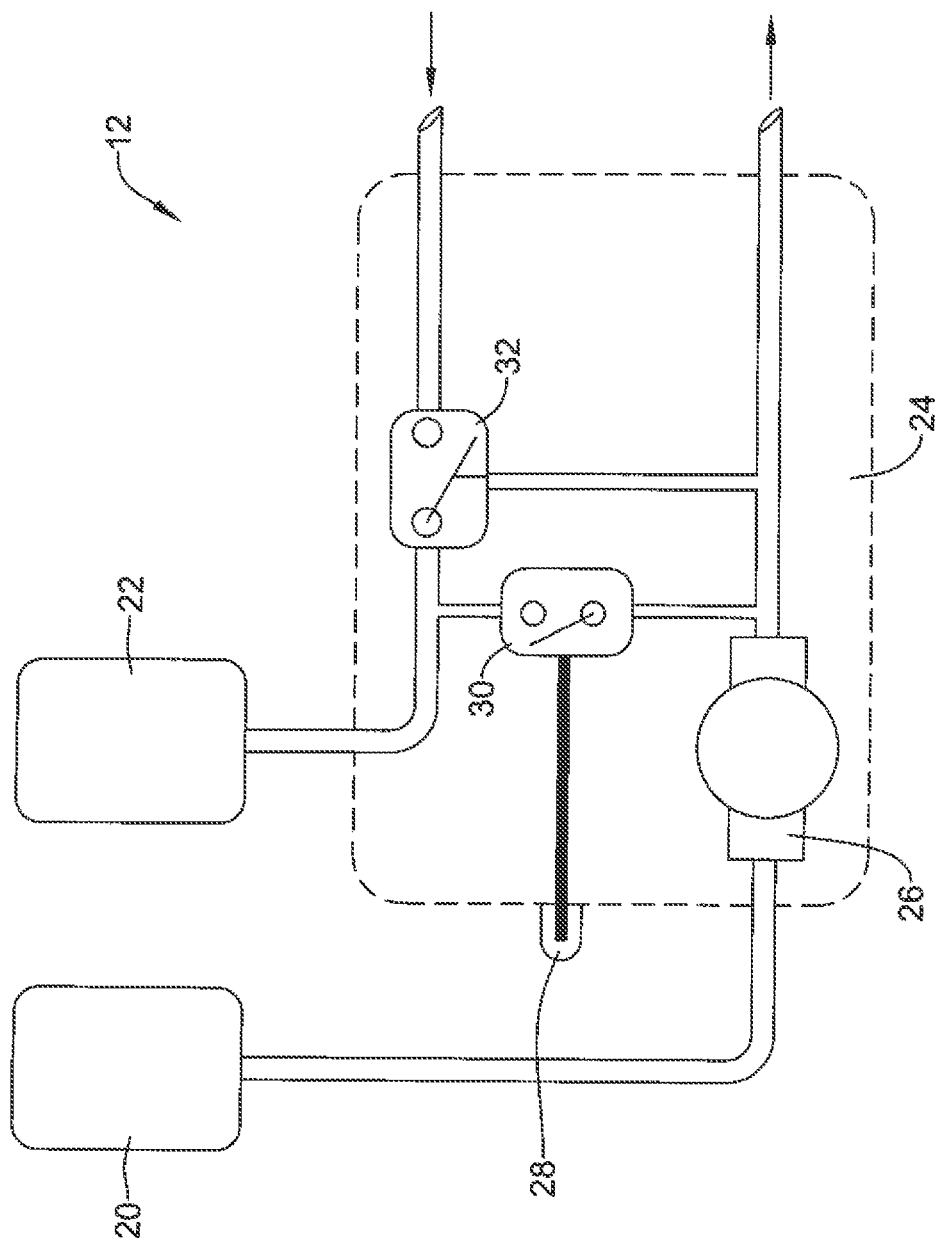
FIG. 2 is a diagrammatic view showing more detail of the proximal portion of assisted catheter aspiration system 10.

FIG. 2 is a diagrammatic view showing more detail of hand piece 12 and the proximal portion of assisted catheter aspiration system 10. Hand piece 12 includes a control box 24 where the power and control systems are disposed. A pump 26 may be motor driven displacement pump that has a constant output of less than 30% of the total aspiration volume, based on the minimum catheter dimensions. This pump displacement to catheter volume ensures that no energy is transferred to the patient from the saline pump as all pressurized fluid is evacuated by the aspiration lumen. A prime button 28 is mechanically connected to a prime valve 30. When preparing the device for use, it is advantageous to evacuate all air from the pressurized fluid system to reduce the possibility of air embolization. By depressing prime button 28, the user connects fluid source 20 to vacuum source 22 via the pump 26. This forcefully pulls fluid through the entire pump system, removing all air and positively primes the system for safe operation. A pressure/vacuum valve 32 is used to turn the vacuum on and off synchronously with the fluid pressure system. One contemplated valve 32 is a ported one way valve. Such a valve is advantageous with respect to manual or electronic valve systems because it acts as a tamper proof safety feature by mechanically and automatically combining the operations of the two primary systems. By having pressure/vacuum valve 32, the possibility of turning the vacuum on without activating the fluid system is eliminated.

An electronic control board (not shown) is used to provide the operator interface by use of switches and indicator lamps. The control board also monitors and controls several device safety functions, which include over pressure and air bubble detection and vacuum charge. In one contemplated embodiment, the pump pressure is proportional to the electric current needed to produce that pressure. Consequently, if the electric current required by pump 26 exceeds a preset limit, the control board will disable the pump by cutting power to it. Air bubble detection may also be monitored by electrical current going to the pump. In order for a displacement pump to reach high fluid pressures, there should be little or no air (which is highly compressible) present in the pump or connecting system. The fluid volume is small enough that any air in the system will result in no pressure being generated at the pump head. The control board monitors the pump current for any abrupt downward change that may indicate that air has entered the system. If the rate of drop is faster than a preset limit, the control board will disable the pump by cutting power to it until the problem is corrected. The vacuum line may be connected to a negative pressure sensor. If the vacuum is vacuum source 22 is low or if a leak is detected in the vacuum system, the control board disables the pump until the problem is corrected. The vacuum sensor may also be part of the safety circuit that will not allow the pump to run if vacuum is not present. Thereby a comprehensive safety system that requires both pump pressure and vacuum pressure for the system to run. If a problem exists, the control board will not allow the user to operate the device until all problems are corrected.

Figure 3:
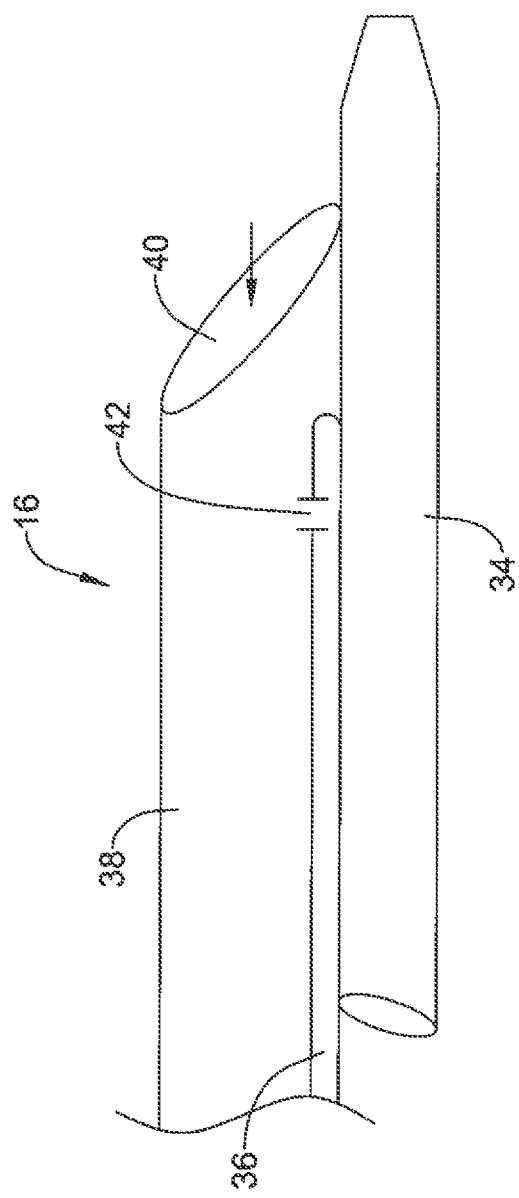
FIG. 3 is a diagrammatic view of the distal end portion of assisted catheter aspiration system 10.

FIG. 3 is a diagrammatic view of the distal end portion of assisted catheter aspiration system 10, showing more details of catheter 16. Catheter 16 is a single-operator exchange catheter and includes a short guidewire lumen 34 attached to the distal end of the device. Guidewire lumen can be between 1 and 30 cm in length, more preferable between 5 and 25 cm in length, or between 5 and 20 cm in length, or approximately 15 cm in length. Aspiration lumen 38 includes a distal opening 40 to allow the vacuum to draw thrombetic material into the lumen. A high pressure lumen 36 includes a distal orifice 42 that is set proximally of distal opening 40 by a set amount. For example, distal orifice 42 can be set proximally of distal opening 40 by about 0.020", more preferably by 0.020"+−0.003" or by another desired amount. Orifice 42 is configured to spray across the aspiration lumen to dilute the thrombetic material for transport to vacuum source 22. The axial placement of the fluid orifice 42 is such that the spray pattern interaction with the opposing lumen wall preferably produces a spray mist and not a swirl pattern that could force embolic material out from the distal opening 40. The irrigation fluid preferably leaves orifice 42 at between 200 and 450 psi and more preferably at between 250 and 300 psi.

Other contemplated catheters are disclosed in co-pending application Ser. No. 12/026,317 to Jensen et al., entitled "Thrombectomy Apparatus and Method" and filed Feb. 5, 2008, which is incorporated by reference.

In some cases, parts or all of the devices described herein may be doped with, made of, coated with, or otherwise include a radiopaque material. Radiopaque materials are understood to be materials capable of producing a relatively bright image on a fluoroscopy screen or another imaging technique during a medical procedure. Some examples of radiopaque materials can include, but are not limited to, gold, platinum, palladium, tantalum, tungsten alloy, polymer material loaded with a radiopaque filler, and the like.

In some instances, a degree of MRI compatibility may be imparted into parts of the devices described herein. For example, to enhance compatibility with Magnetic Resonance Imaging (MRI) machines, it may be desirable to make various portions of the devices described herein from materials that do not substantially distort MRI images or cause substantial artifacts (gaps in the images). Some ferromagnetic materials, for example, may not be suitable as they may create artifacts in an MRI image. In some cases, the devices described herein may include materials that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some instances, some of the devices described herein may include a coating such as a lubricious coating or a hydrophilic coating. Hydrophobic coatings such as fluoropolymers provide a dry lubricity. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

Reference Numeral List

10 Assisted Aspiration Catheter System
12 Hand Piece
14 Extension Tubing
16 Catheter
18 Connector
20 Fluid Source
22 Vacuum Source
24 Control Box
26 Pump
28 Prime Button
30 Prime Valve
32 Pressure/Vacuum Valve
34 Guidewire Lumen
36 High Pressure Lumen
38 Aspiration Lumen
40 Distal Opening
42 Orifice

The invention claimed is:

1. A thrombectomy system, comprising
an aspiration catheter having an aspiration lumen and a high pressure irrigation lumen, the aspiration catheter having a proximal end and a distal end;
a control box adapted to be connected to the aspiration lumen and the high pressure irrigation lumen of the aspiration catheter;
a displacement pump;
wherein the control box is configured to signal the displacement pump to provide pulses of high pressure irrigation fluid from a fluid source in a sinusoidal pressure pattern to the high pressure irrigation lumen when vacuum from a vacuum source is present in the aspiration lumen, and to prevent the high pressure irrigation fluid from the fluid source from being provided to the high pressure irrigation lumen when the vacuum from the vacuum source is not present in the aspiration lumen;
wherein the aspiration lumen has a distal opening and wherein the high pressure irrigation lumen has a distal orifice directed into the aspiration lumen and configured to release a jet of irrigation fluid across a width of the aspiration lumen against an opposing wall of the aspiration lumen, wherein the distal orifice is proximal of the distal opening; and
wherein the jet forms a spray pattern that interacts with the opposing wall of the aspiration lumen in such a way that embolic material is diluted for aspiration and not forced out of the distal opening.

2. The thrombectomy system of claim 1, wherein the distal orifice is proximal of the distal opening by at least 0.050 cm.

3. The thrombectomy system of claim 1, wherein the distal orifice is proximal of the distal opening by between 0.043 cm and 0.058 cm.

4. The thrombectomy system of claim 1, further comprising a control board configured to cut power to the pump when a sensed current at the pump is out of a predetermined range.

5. The thrombectomy system of claim 1, further comprising a control board configured to cut power to the pump when a sensed current at the pump drops faster than a preset limit.

6. The thrombectomy system of claim 1, wherein the vacuum source is a vacuum bottle.

7. The thrombectomy system of claim 1, wherein the fluid source is a saline bag.

8. The thrombectomy system of claim 1, further comprising extension tubing fluidly connecting the control box to the aspiration lumen and the high pressure irrigation lumen of the aspiration catheter.

9. The thrombectomy system of claim 8, wherein the extension tubing is configured to dampen the pulses of high pressure irrigation fluid provided by the pump.

10. The thrombectomy system of claim 9, wherein the extension tubing comprises a compliant material.

11. The thrombectomy system of claim 1, wherein the distal orifice is further configured such that the jet of irrigation fluid is released normal to a longitudinal axis of the aspiration lumen.

12. The thrombectomy system of claim 1, wherein the distal orifice is further configured such that the jet of irrigation fluid has a spray mist pattern.

13. The thrombectomy system of claim 1, wherein the sinusoidal pressure pattern comprises distinct variations between peaks and valleys in each sine wave.

14. The thrombectomy system of claim 1, wherein the control box includes a pressure/vacuum valve interposed along the aspiration lumen between the vacuum source and the distal opening and configured to cause the vacuum source to be turned on and off.

15. The thrombectomy system of claim 14, wherein the control box responds to irrigation fluid supplied to a first passage within the control box by opening a second passage within the control box which is connected to the aspiration lumen.

16. The thrombectomy system of claim 15, wherein the pressure/vacuum valve is a mechanical valve such that fluid pressure in the first passage operates the pressure/vacuum valve.

17. The thrombectomy system of claim 15, wherein the pressure/vacuum valve is controlled electronically.

18. The thrombectomy system of claim 15, further comprising a control board configured to cut power to the pump when a sensed vacuum pressure at the second passage is out of a determined range.

19. The thrombectomy system of claim 15, further comprising a priming valve fluidly connecting the first passage and the second passage when opened.

20. A method of removing a thrombus, comprising:
providing an aspiration catheter having an aspiration lumen and a high pressure irrigation lumen, the aspiration catheter having a proximal end and a distal end;
providing a control box adapted to be connected to the aspiration lumen and the high pressure irrigation lumen of the aspiration catheter;
providing a displacement pump, wherein the control box is configured to signal the displacement pump to provide pulses of high pressure irrigation fluid from a fluid source in a sinusoidal pressure pattern to the high pressure irrigation lumen when vacuum from a vacuum source is present in the aspiration lumen, and to prevent the high pressure irrigation fluid from the fluid source from being provided to the high pressure irrigation lumen when the vacuum from the vacuum source is not present in the aspiration lumen, wherein the aspiration lumen has a distal opening and wherein the high pressure irrigation lumen has a distal orifice directed into the aspiration lumen and configured to release a jet of irrigation fluid across a width of the aspiration lumen against an opposing wall of the aspiration lumen, wherein the distal orifice is proximal of the distal opening, and wherein the jet forms a spray pattern that interacts with the opposing wall of the aspiration lumen in such a way that embolic material is diluted for aspiration and not forced out of the distal opening;
inserting the aspiration catheter into the vasculature of a patient;
advancing the aspiration catheter to a region of interest; and
operating the control box to synchronously provide high pressure irrigation fluid and aspiration through the aspiration catheter to draw the thrombus into the aspiration lumen.

* * * * *